(12) United States Patent
Mogna

(10) Patent No.: US 10,933,105 B2
(45) Date of Patent: *Mar. 2, 2021

(54) COMPOSITION FOR USE AS A SUPPORT THERAPY FOR TREATMENT OF TUMOURS, AIDS AND LEUKAEMIA

(71) Applicant: Giovanni Mogna, Novara (IT)

(72) Inventor: Giovanni Mogna, Novara (IT)

(73) Assignees: Chiara Benassai, Novara (IT); Elena Mogna, Novara (IT); Vera Mogna, Novara (IT)

(*) Notice: Subject to any disclaimer, the term of this patent is extended or adjusted under 35 U.S.C. 154(b) by 133 days.

This patent is subject to a terminal disclaimer.

(21) Appl. No.: 14/758,211

(22) PCT Filed: Dec. 31, 2013

(86) PCT No.: PCT/IB2013/002890
§ 371 (c)(1),
(2) Date: Jun. 26, 2015

(87) PCT Pub. No.: WO2014/102595
PCT Pub. Date: Jul. 3, 2014

(65) Prior Publication Data
US 2015/0343004 A1 Dec. 3, 2015

(30) Foreign Application Priority Data
Dec. 31, 2012 (IT) .............................. MI2012A2270

(51) Int. Cl.
| A61K 35/747 | (2015.01) |
| A61P 35/02 | (2006.01) |
| A61P 37/04 | (2006.01) |
| A61P 35/00 | (2006.01) |
| A61P 31/18 | (2006.01) |

(52) U.S. Cl.
CPC ............ *A61K 35/747* (2013.01); *A61P 31/18* (2018.01); *A61P 35/00* (2018.01); *A61P 35/02* (2018.01); *A61P 37/04* (2018.01)

(58) Field of Classification Search
CPC ........ A61K 36/747; A61P 13/18; A61P 35/00; A61P 35/02; A61P 35/3704
See application file for complete search history.

(56) References Cited

U.S. PATENT DOCUMENTS

| 5,292,511 A * | 3/1994 | Kim ......................... A23L 27/24 424/744 |
| 2004/0175389 A1* | 9/2004 | Porubcan ............. A61K 35/747 424/184.1 |
| 2006/0045887 A1* | 3/2006 | Mahajna ................. A61K 36/07 424/195.15 |
| 2006/0127482 A1* | 6/2006 | Fewell ................. A61K 9/0019 424/486 |
| 2006/0134238 A1* | 6/2006 | Dnyaneshwar ...... A61K 36/886 424/744 |
| 2011/0027230 A1* | 2/2011 | Di Leo .................. A61K 31/05 424/93.1 |
| 2011/0117210 A1* | 5/2011 | Ugolkov .............. A61K 31/315 424/643 |
| 2012/0052050 A1 | 3/2012 | Dondi et al. |
| 2014/0296179 A1 | 10/2014 | Boehm et al. |
| 2015/0343004 A1 | 12/2015 | Mogna |
| 2020/0197453 A1 | 6/2020 | Mogna |

FOREIGN PATENT DOCUMENTS

| EP | 08789404 | 4/2010 |
| EP | 2938349 B1 | 2/2018 |
| EP | 3345611 A1 | 7/2018 |
| RU | 2385725 C2 | 4/2010 |
| RU | 2415920 C2 | 4/2011 |
| RU | 2015124336 A | 2/2017 |
| WO | 2009/013709 | 1/2009 |
| WO | 2010/136891 | 12/2010 |
| WO | 2011/110918 | 9/2011 |

OTHER PUBLICATIONS

Clerici et al. Annals New York Academy Sci. (2000) 917 (Neuroimmunomodulation): 956-961.*
Lissoni et al. In vivo (2009) 23:171-176.*
Becker, Y. Anticancer Research (2006) 26: 1113-1134.*
Mitchell et al. Cancer Immunol. Immunother.(2003) 52: 686-692 (Year: 2003).*
PCT International Search Report dated Mar. 17, 2014 for PCT/IB2013/002890 filed on Dec. 31, 2013 in the name of Giovanni Mogna.
PCT Written Opinion dated Mar. 17, 2014 for PCT/IB2013/002890 filed on Dec. 31, 2013 in the name of Giovanni Mogna.
International Preliminary Report on Patentability for PCT/IB2013/002890 filed Dec. 31, 2013 on behalf of Giovanni Mogna, dated Jul. 9, 2015. 8 pages.
Search Report with English translation for Russian Application No. 2015124336 filed on Dec. 31, 2013 on behalf of Giovanni Mogna, dated Mar. 15, 2017. 4 pages.
Office Action with English translation for Russian Application No. 2015124336 filed on Dec. 31, 2013 on behalf of Giovanni Mogna, dated Apr. 18, 2017. 10 pages.
Office Action with English translation for Chinese Application No. 201380068989.3 filed Dec. 31, 2013 on behalf of Giovanni Mogna, dated May 23, 2018. 10 pages.

(Continued)

*Primary Examiner* — Susan M Hanley
(74) *Attorney, Agent, or Firm* — Steinfl + Bruno, LLP

(57) ABSTRACT

Described in the instant application are methods and compositions for support therapy in antitumor chemotherapeutic treatments, in acquired immunodeficiency syndrome treatments and in leukemia treatments. Said methods and compositions comprise a bacterial strain belonging to the species *Lactobacillus pentosus* and having an antiviral and an antibacterial activity, and a highly bioavailable zinc internalized in a tyndalized bacterial cell mixed with at least one rubber, and in particular an alginate and/or a gel, and in particular a gel.

4 Claims, No Drawings

(56) References Cited

OTHER PUBLICATIONS

Search Report with English translation for Chinese Application No. 201380068989.3 filed Dec. 31, 2013 on behalf of Giovanni Mogna, dated May 15, 2018. 8 pages.
Brazilian First Office Action BZ112015015393-3 in the name of Giovanni Mogna filed on Dec. 31, 2013, including English Translation, 5 pages, dated Aug. 13, 2019.
Chinese Decision for Rejection for Chinese Application No. 201380068989.3, dated Mar. 3, 2020. 5 pages. (English + Chinese Translation).
Korean Office Action for Korean Application No. 10-2015-7020418, dated Apr. 27, 2020. 5 pages. (English + Korean).
Canadian Examination report for CN 2,896,402 filed in the name of Giovanni Mogna. dated Jul. 6, 2020. 3 pages.
Notice of Allowance for Korean Application No. 10-2015-7020418 filed in the name of Giovanni Mogna, dated Sep. 2, 2020. Korean and English translation. 3 pages.
Chinese Office Action with English translation for Application No. CN 201380068989.3 filed on Dec. 31, 2013 on behalf of Giovanni Mogna, dated Oct. 13, 2020. 5 pages. Original and English.

\* cited by examiner

COMPOSITION FOR USE AS A SUPPORT THERAPY FOR TREATMENT OF TUMOURS, AIDS AND LEUKAEMIA

CROSS REFERENCE TO RELATED APPLICATIONS

The present application is the US national stage of International Patent Application PCT/IB2013/002890 filed on Dec. 31, 2013, which, in turn, claims priority to Italian Patent Application MI2012A002270 filed on Dec. 31, 2012.

The present invention relates to a composition for use as support therapy in antitumor chemotherapeutic treatments, in acquired immunodeficiency syndrome treatments and in leukemia treatments. Said composition comprising a bacterial strain belonging to the species *Lactobacillus pentosus* and having an antiviral and an antibacterial activity and a highly bioavailable zinc internalized in a tyndalized bacterial cell mixed with at least one rubber, preferably an alginate and/or a gel, preferably a gel.

Chemotherapy is known to result in a reduction of the immune system activity and a deficit immune system cannot protect the organism from bacterial and viral infections.

Moreover, chemotherapy (chemo) is known to have a prevailing effect on the tumor but, unfortunately, it also has side-effects on healthy tissues, on all tissues, although mainly on some of them such as the intestine causing mucositis, nausea, vomiting, diarrhea, alimentation difficulty and thus malnutrition.

It would not be possible to administer effective chemotherapy doses unless a therapy which can contrast—of course within certain limits—the adverse effects of chemotherapy by means of a support therapy were implemented.

Thus, there is still the need to have a support therapy to chemotherapy, in particular a support therapy for the damages caused to esophagus, stomach and intestine mucosae, and it is therefore absolutely necessary to have these mucosae be suitably protected.

Moreover, there is still the need to have a support therapy to chemotherapy, in particular a support therapy to the immune system since chemotherapy implies a reduction of the effectiveness of the immune system, which results in a vulnerability of the organism to bacteria and viruses causing the occurrence of bacterial and viral infections.

After a long and deep research activity, the Applicant has identified and selected a bacterial strain with a strong antiviral activity. The bacterial strain selected by the Applicant, beyond a remarkable antiviral activity, has a strong antibacterial activity since it can produce bacteriocins and/or hydrogen peroxide and/or metabolites with an antibacterial activity.

Therefore, the strain selected by the Applicant is unique since it can exert an antiviral and an antibacterial activity at the same time.

The bacterial strain selected by the Applicant shows a remarkable stimulating activity on the immune system resulting in the endogenous production of interleukin 17, in particular interleukin 17A (IL-17A) and gamma-interferon.

Interleukin IL-17A can exert a vascularizing activity for vessels in the regions where tumor cells are located. A stronger blood circulation or vascularization in the vessels allows to inhibit the production of metastasis since tumor cells are more localized and coherent. Moreover, the aforesaid proangiogenic effect allows chemotherapeutic treatments to better penetrate the tumor mass and allows treatments to be more effective and localized. Moreover, gamma-interferon has an antiviral capacity.

The Applicant has found out that the selected bacterial strain can activate and stimulate the immune system (IS) so as to cause a higher endogenous production of interleukin 17, in particular interleukin 17A (IL-17A) and gamma-interferon.

An object of the present invention is a bacterial strain belonging to the species *Lactobacillus pentosus* having an antiviral activity (cytokine production) and an antibacterial activity (bacteriocin production).

In one embodiment, the bacterial strain belonging to the species *Lactobacillus pentosus* and having an antiviral and an antibacterial activity is the strain *Lactobacillus pentosus* LPS01 with number of deposit DSM 21980, deposited on Nov. 14, 2008 by Probiotical SpA in compliance with the Budapest Treaty.

Moreover, the Applicant has found out that IS activation can be carried out by means of a zinc with a very high bioavailability obtained with a zinc internalized in a tyndalized bacterial cell, which cell belongs to a strain belonging to the species *B. lactis*, preferably the strain *Bifidobacterium lactis* Bb 1 DSM 17850 deposited in the DSMZ on Dec. 23, 2005, which is the object of European Patent Application no. 08789404 herein incorporated as reference. The address of DSMZ (Deutsche Sammlung von Mikroorganismen und Zellkulturen GmbH) is Inhoffenstrasse 7B, D-38124 Braunschweig, Germany.

In practice, the Applicant has found out that highly bioavailable zinc internalized in a tyndalized (inactivated) cell activates the IS, in particular the thymus which is appointed to produce T-lymphocytes producing non-toxic endogenous cytokines such as interleukin IL-17A and gamma-interferon. This mechanism as a whole is activated thanks to the bacterial strain *Lactobacillus pentosus* LPS01 with number of deposit DSM 21980.

The strain *Lactobacillus pentosus* LPS01 with number of deposit DSM 21980 is suitable for the treatment of infections caused by gram-negative bacteria such as enterococci, coliforms and *E. coli*. As a matter of fact, the strain *Lactobacillus pentosus* LPS01 DSM 21980 was successfully tested, by producing hydrogen peroxide, bacteriocins and metabolites, against the following target pathogens *E. coli* ATCC 8739, *E. coli* ATCC 10536, *E. coli* ATCC 35218 and *E. coli* ATCC 25922 with a charge of about $1 \times 10^8$ CFUs/g.

The strain *Lactobacillus pentosus* LPS01 with number of deposit DSM 21980 was tested in order to evaluate its ability to modulate in-vitro proliferation and release of cytokines from PBMC cells from healthy donors. PBMC cells were isolated from human peripheral blood and co-cultured with the strain *Lactobacillus pentosus* LPS01 DSM 21980. The specific stimulation of different populations of immune cells and the secretion of endogenous cytokines were monitored by means of FACS and ELISA, respectively. The results having a statistical value show that the strain *Lactobacillus pentosus* LPS01 DSM 21980 induces a remarkable secretion of endogeous Th1 cytokines with a strong increase for IL-17A (Table A) and for IFN-γ (Table B).

The dosage of IL-17A cytokine was made on supernatants from PBMC cultures stimulated with three single bacterial strains: *L. salivarius* DLV1 DSM 25138, *L. salivarius* LS01 DSM 22775 and *L. pentosus* LPS01 DSM 21980, after 5 days of culture. The results having a statistical value, expressed as IL-17A (pg/ml), are shown in Table A below.

TABLE A

| | IL-17A (pg/ml) |
|---|---|
| Basal | 13 |
| DLV1 | 12 |
| LS01 | 10 |
| LPS01 | 41 |

The three bacterial strains as analyzed showed a different ability to modulate IL-17A cytokine, in particular there is no effect for *L. salivarius* DLV1 DSM 25138 and *L. salivarius* LS01 DSM 22775, whereas for *L. pentosus* LPS01 DSM 21980 this has highly increased the secretion of IL-17A with respect to basal conditions (Basal).

The dosage of gamma-interferon was made on PBMCs isolated from human peripheral blood and co-cultured with the strain *L. plantarum* LP01 (LMG P-21021) and with the strain *L. pentosus* LPS01 DSM 21980. The results having a statistical value, expressed as IFN-gamma (pg/ml), are shown in Table B below.

TABLE B

| | IFN-gamma (pg/ml) |
|---|---|
| Control | 150 |
| LP01 | 210 |
| LPS01 | 1550 |

The strain *L. pentosus* LPS01 DSM 21980 shows a 10-time higher ability to stimulate gamma-interferon than the control.

Advantageously, the production of endogenous cytokines does not involve toxicity unlike exogenous cytokines administered by infusion.

An object of the present invention is a pharmaceutical composition or a food composition or a composition including a food supplement or a composition including a medical device (hereinafter referred to as the composition according to the present invention), having the characteristics as claimed in the attached claim.

Said composition according to the present invention usefully applies as support therapy in antitumor chemotherapeutic treatments, in acquired immunodeficiency syndrome treatments and in leukemia treatments.

The composition according to the present invention comprises a rubber, preferably an alginate or a derivative thereof and/or a gel, preferably an *Aloe* gel or a derivative thereof.

The alginate or derivative thereof is preferably a sodium alginate.

The *Aloe*-based product or derivative thereof is preferably *Aloe arborescens*; preferably in lyophilized form.

*Aloe arborescens* is preferably in lyophilized form.

Both the alginate and the *Aloe*-based product, once they get in contact with saliva or with water used for swallowing the tablet or capsule or for dissolving the granule or powder composition, can give rise to a gel.

The alginate or the *Aloe*-based product in gel form can have a mechanical effect or protect mucosae in the esophagus, stomach and gastro-intestinal tract.

The alginate, preferably sodium alginate, has a mechanical anti-regurgitation, anti-esophagitis and anti-gastritis activity and can make the side-effects of a chemotherapeutic treatment more tolerable to patients suffering from tumor diseases.

The *Aloe*-based product, preferably *Aloe arborescens* in lyophilized form, has a mechanical function of physical protection of esophagus, stomach and intestine mucosae. Moreover, the *Aloe*-based product, preferably *Aloe arborescens* in lyophilized form and reconstituted in gel form, can reduce the adhesive capacity of pathogenic strains, in particular of flagellated pathogenic strains both in the esophagus and in the gastro-intestinal tract. Finally, the *Aloe*-based product, preferably *Aloe arborescens* in lyophilized form and reconstituted in gel form, can reduce gastric and intestinal permeability.

The *Aloe*-based product, preferably *Aloe arborescens* in lyophilized form and reconstituted in gel form, by coating the esophagus, stomach and intestine mucosae and by reducing the adhesive capacity of flagellated pathogens, can make the side-effects (bacterial infections) of a chemotherapeutic treatment more tolerable to patients suffering from tumor diseases.

In one embodiment, the composition according to the present invention comprises sodium alginate and *Aloe arborescens* in lyophilized form in a weight ratio of 1:50 (alginate:*Aloe*) to 50:1, preferably of 1:30 (alginate:*Aloe*) to 30:1.

Said composition according to the present invention further comprises some bacterial strains in association with alginate, preferably sodium alginate, and/or the *Aloe*-based product, preferably *Aloe arborescens* in lyophilized form.

In one embodiment, the composition according to the present invention comprises in association with alginate, preferably sodium alginate, and/or the *Aloe*-based product, preferably *Aloe arborescens* in lyophilized form, a bacterial strain belonging to the species *Lactobacillus pentosus* having an antiviral and an antibacterial activity; said strain being the strain *Lactobacillus pentosus* LPS01 with number of deposit DSM 21980, deposited on Nov. 14, 2008 by Probiotical SpA.

In another embodiment, the composition according to the present invention comprises in association with alginate, preferably sodium alginate, and/or the *Aloe*-based product, preferably *Aloe arborescens* in lyophilized form, the bacterial strain *Lactobacillus pentosus* LPS01 DSM 21980 in association with a highly bioavailable zinc internalized in a tyndalized bacterial cell.

The Applicant has selected some bacterial strains which can make zinc highly bioavailable (internalized) in the form of a tyndalized (inactivated) cell. Zinc in this form is highly bioavailable and as such can be assimilated more easily by the organism. The zinc ion made bioavailable and easily assimilable by the organism plays an important role and an action towards the thymus, which is responsible for the formation/production of lymphocytes.

Said bacterial strain internalizing the zinc ion is selected from the group comprising or, as an alternative, made up of the strain *Streptococcus thermophilus* ST16 BM DSM 19526 deposited in the DSMZ on Jul. 13, 2007 and of the strain *Bifidobacterium lactic* Bb 1 DSM 17850 deposited in the DSMZ on Dec. 23, 2005.

In another embodiment, the composition comprises, in association with alginate, preferably sodium alginate, and/or the *Aloe*-based product, preferably *Aloe arborescens* in lyophilized form, the bacterial strain *Lactobacillus pentosus* LPS01 DSM 21980 in association with a highly bioavailable zinc internalized in a tyndalized bacterial cell selected from the group comprising or, as an alternative, made up of the strain *Streptococcus thermophilus* ST16 BM DSM 19526 deposited in the DSMZ on Jul. 13, 2007 and of the strain *Bifidobacterium lactic* Bb 1 DSM 17850 deposited in the DSMZ on Dec. 23, 2005.

An object of the present invention is a composition for use as support therapy in antitumor chemotherapy treatments, in acquired immunodeficiency syndrome treatments and in leukemia treatments; said composition comprising the bacterial strain *Lactobacillus pentosus* LPS01 with number of deposit DSM 21980, deposited on Nov. 14, 2008 by Probiotical SpA. The composition comprises said strain in an amount of $1\times10^8$ to $1\times10^{11}$ CFUs/g of composition.

In one embodiment, said composition further comprises a highly bioavailable zinc internalized in a tyndalized bacterial cell. Preferably, said tyndalized bacterial cell is selected from the group comprising the strain *Streptococcus thermophilus* ST16 BM DSM 19526 deposited in the DSMZ on Jul. 13, 2007 and the strain *Bifidobacterium lactic* Bb 1 DSM 17850 deposited in the DSMZ on Dec. 23, 2005.

In another embodiment, said composition further comprises at least one rubber, preferably a vegetable rubber. Preferably, said vegetable rubber is at least one alginate, preferably sodium alginate.

In another embodiment, said composition further comprises at least one gel. Preferably, said gel is an *Aloe* gel, preferably an *Aloe arborescens* gel. Still more preferably, said *Aloe* gel is an *Aloe arborescens* gel in lyophilized form.

In one embodiment, said composition comprises the bacterial strain *Lactobacillus pentosus* LPS01 with number of deposit DSM 21980; at least one bacterial strain internalizing the zinc ion, selected from the group comprising the strain *Streptococcus thermophilus* ST16 BM with number of deposit DSM 19526 and the strain *Bifidobacterium lactic* Bb 1 with number of deposit DSM 178505; an alginate, preferably a sodium alginate and a product based on *Aloe arborescens*, preferably in lyophilized form.

The invention claimed is:

1. A method to treat a subject receiving antitumor chemotherapy, the method comprising
    administering to the subject a composition comprising bacterial strain *Lactobacillus pentosus* LPS01 with number of deposit DSM 21980, deposited on Nov. 14, 2008 by Probiotical SpA in amount of $1\times10^8$ to $1\times10^{11}$ CFUs/g of the composition as a support therapy in said antitumor chemotherapeutic treatments, wherein said composition further comprises zinc internalized in a tyndalized bacterial strain.

2. The method according to claim 1, wherein said tyndalized bacterial strain is selected from strain *Streptococcus thermophilus* ST16 BM DSM 19526 deposited in the DSMZ on Jul. 13, 2007 and strain *Bifidobacterium lactic* Bb 1 DSM 17850 deposited in the DSMZ on Dec. 23, 2005.

3. The method according to claim 1 wherein said composition further comprises at least one rubber.

4. The method of claim 1, wherein said composition comprises the bacterial strain *Lactobacillus pentosus* LPS01 with number of deposit DSM 21980; at least one bacterial strain internalizing the zinc ion, selected from the group comprising the strain *Streptococcus thermophilus* ST16 BM with number of deposit DSM 19526 and the strain *Bifidobacterium lactic* Bb 1 with number of deposit DSM 17850; an alginate, and a product based on *Aloe arborescens*.

\* \* \* \* \*